United States Patent [19]

Zoeller et al.

[11] Patent Number: 4,752,897

[45] Date of Patent: Jun. 21, 1988

[54] SYSTEM FOR MONITORING AND ANALYSIS OF A CONTINUOUS PROCESS

[75] Inventors: Leon R. Zoeller, Hamlin; Roger E. Button, Rochester; Louis R. Gabello, Rochester; Joseph P. DiVincenzo, Rochester; Thomas O. Lange, Rochester, all of N.Y.

[73] Assignee: Eastman Kodak Co., Rochester, N.Y.

[21] Appl. No.: 45,357

[22] Filed: May 1, 1987

[51] Int. Cl.$^4$ ............................................. G06F 15/20
[52] U.S. Cl. .................................... 364/550; 250/563; 382/16; 382/56
[58] Field of Search .................. 250/559, 561–563; 382/10, 16, 18, 19, 20, 22, 23, 26, 56, 57; 364/550–552, 571

[56] References Cited

U.S. PATENT DOCUMENTS

| | | | |
|---|---|---|---|
| 3,866,054 | 2/1975 | Wolf | 250/562 |
| 3,868,635 | 2/1975 | Shah et al. | 382/18 |
| 3,958,127 | 5/1976 | Faulhaber | 250/563 |
| 3,970,857 | 7/1976 | Buckson | 250/563 |
| 4,149,089 | 4/1979 | Idelsohn | 250/563 |
| 4,166,541 | 9/1979 | Smith | 209/587 |
| 4,242,662 | 12/1981 | Tsujiyama et al. | 382/8 |
| 4,282,511 | 8/1981 | Southgate | 250/572 |
| 4,302,775 | 11/1981 | Widergren et al. | 382/56 |
| 4,460,273 | 6/1984 | Koizumi | 356/237 |
| 4,493,105 | 1/1985 | Beall et al. | 382/21 |
| 4,541,115 | 9/1985 | Werth | 382/14 |
| 4,546,444 | 10/1985 | Bullis | 364/569 |
| 4,570,074 | 2/1986 | Jette | 250/563 |
| 4,590,606 | 5/1986 | Rohrer | 382/56 |

Primary Examiner—Vit W. Miska
Attorney, Agent, or Firm—Martin LuKacher

[57] ABSTRACT

A continuous process, namely the quality control of web production, is monitored and analyzed for defects with high resolution continuously, notwithstanding that the processing of signals for such continuous monitoring and analysis with high resolution requires handling of data at enormous data rates (e.g., billions of calculations per second). The system uses a computer architecture for continuous processing of the data in real time. In a first level of the architecture, signals arriving from the process (from the scanning of successive lines on the web) are digitized, and reduced to represent data corresponding to certain events, such as defects in the web. In a second level of the architecture, an array of parallel processors operate concurrently and continuously on the reduced data to provide outputs characterizing the events, for example, measurements of the locations and extents of the web defects. In a third level the data from the second level is analyzed to provide outputs representing the analysis of the effects in the process represented by the events. These outputs may be used to control the process or to provide information respecting the source of the defects and otherwise to assure that only high quality material is passed.

18 Claims, 13 Drawing Sheets

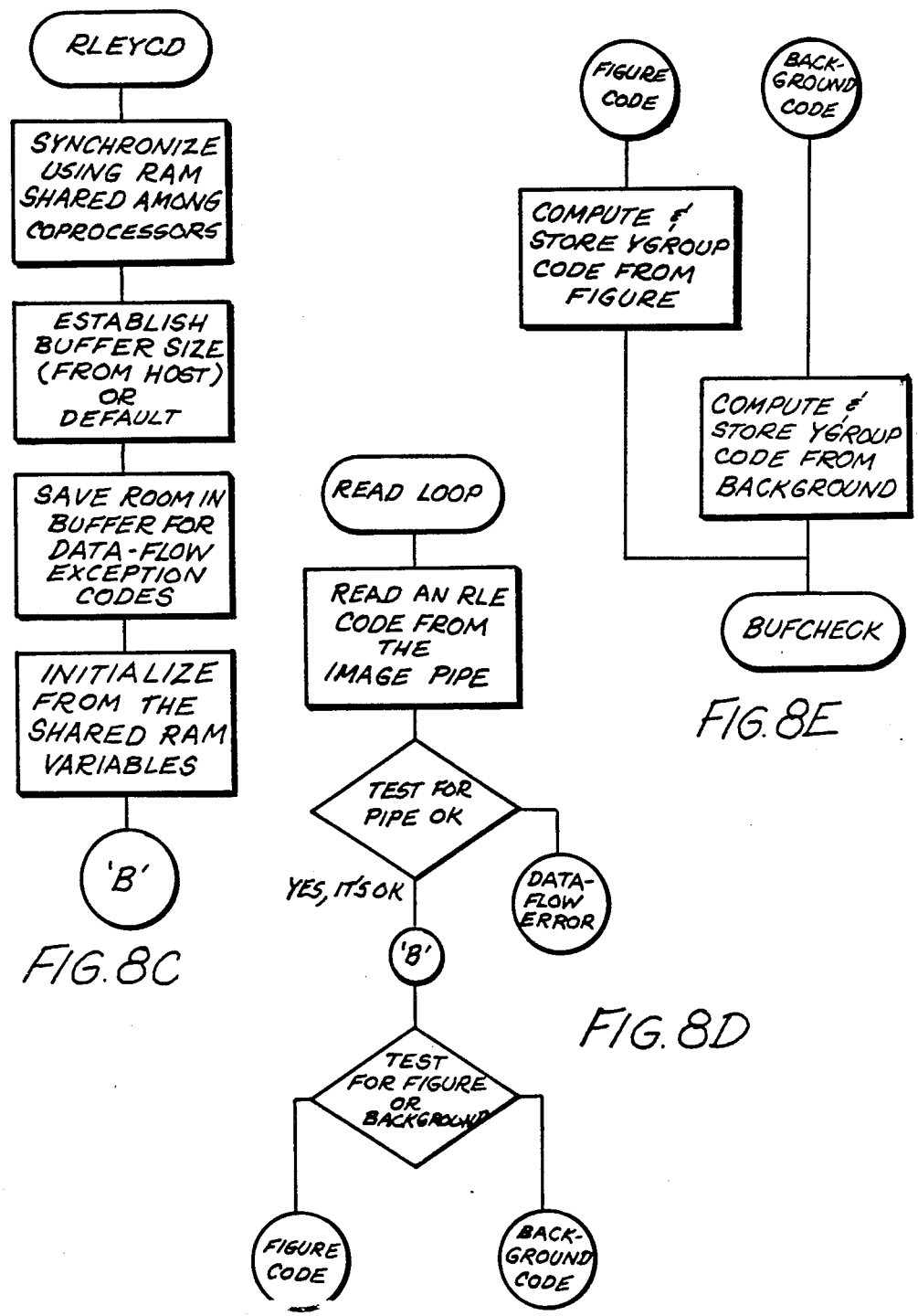

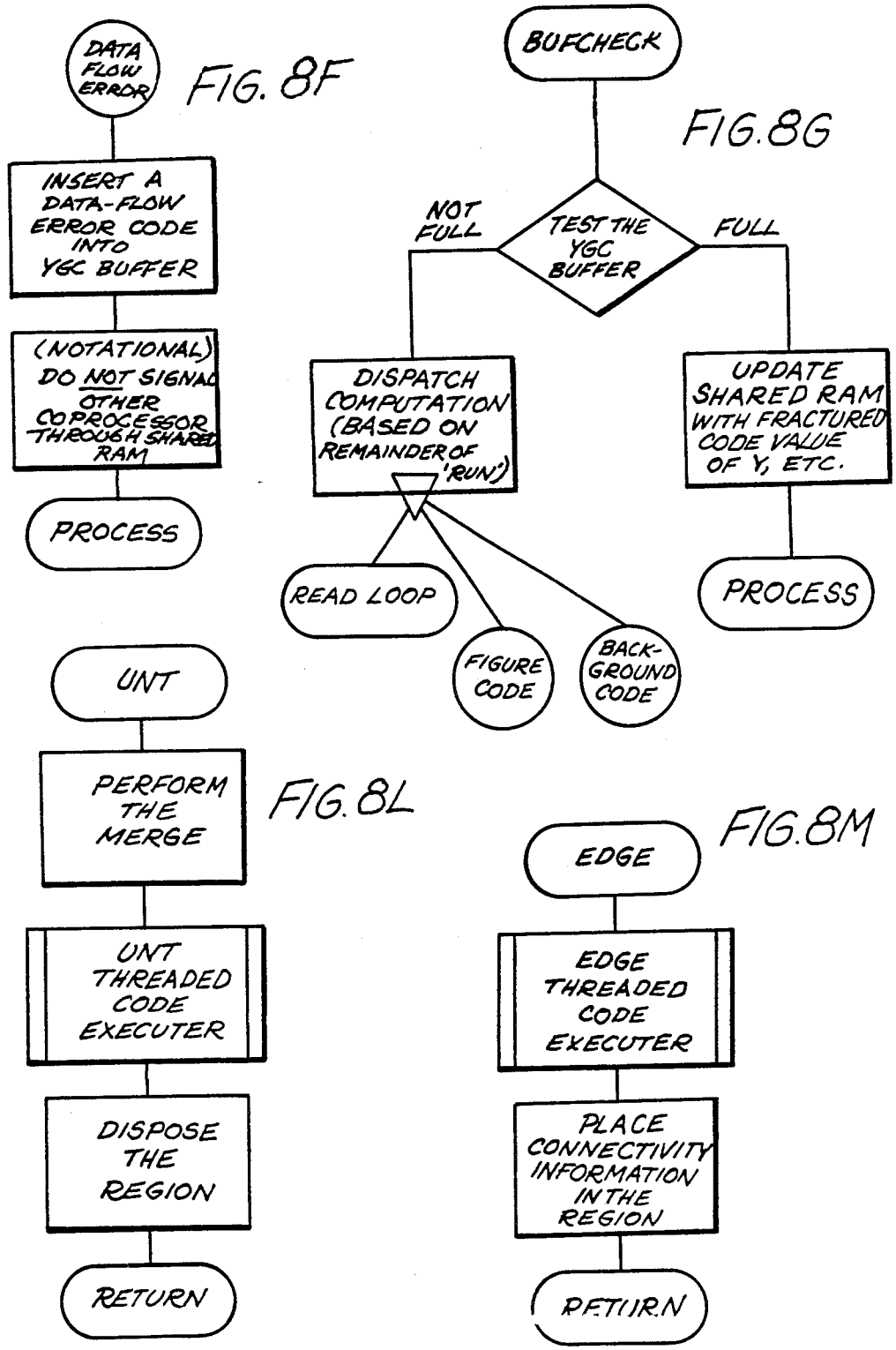

SYSTEM FOR MONITORING AND ANALYSIS OF A CONTINUOUS PROCESS

DESCRIPTION

The present invention relates to systems for the monitoring and analysis of continuous processes which involve the handling of enormous amounts of data, and particularly to, a web defect detection and analysis system with continuous flow processing of high volumes of data for high resolution operation.

The invention is especially suitable for the monitoring and analysis of web production lines for quality control purposes. This system is flexible in providing for measurement and classification analysis of different types of defects simultaneously and in parallel notwithstanding that an enormous amount of data which may require billions of calculations per second is involved in the detection and analysis of the data. The invention is also applicable for the monitoring and analysis of processes, other than web production, which may involve the handling of enormous amounts of data.

Conventionally large amounts of data are handled by dividing the data into frames which are processed off-line and not in real time. Not all of the data necessary for high resolution analysis is used in conventional systems because of the limitations of the computation process. In the case of a moving web, high resolution analysis requires the use of data from closely spaced areas of the web which are very much smaller than the total web surface area which can be very wide and can travel at high speed. As a result, the amount of data which must be handled ranges from 10 to 50 million bytes per second.

Handling of such data on a continuous basis and in real time has not, heretofore, been accomplished (as for example is the case in, U.S. Pat. No. 4,149,089). The patent discloses a computer system in which addresses and classifications for a frame are processed in the computer on a frame-by-frame basis. On-line, real time processing of sufficient data to provide high resolution analysis of the defects is not obtainable with such a system. Other systems process only a limited amount of data which is detected from the web (for example, U.S. Pat. Nos. 4,460,273, 4,248,511, and 4,166,541). Other systems operate on an analog basis and are totally incapable of handling the enormous amounts of data which are necessary for high resolution analysis. See U.S. Pat. Nos. 3,598,127, 3,866,054, 3,970,857, and 4,570,074. In summary, systems which have been proposed and which are capable of operating in real time provide very gross coverage and are not capable of high resolution monitoring and analysis of a process. Other systems operate off-line, and even then provide only gross or partial coverage.

The invention enables a continuous process to be monitored using digital signal processing for handling the enormous quantities of data required for high resolution operation. The invention provides a digital processing architecture which is adapted to handle data from the continuous process continuously and at high data rates. The architecture has a plurality of levels. In the first level, the data is reduced or compressed while being pipelined through a sufficient number of parallel processing channels to enable high resolution measurement and analysis functions to be performed. Data reduction can be accomplished by selection of data representing significant events, for example web imperfections or defects, by enhancing the events and encoding them to the exclusion of other data in a manner to enable location, both spatially and temporally, of the events in the process. In a second level, the compressed data is operated upon by distributed architecture which permits operations to be distributed along the data flow path serially and/or in parallel with other like or unlike operations. For example, an array or arrays containing pluralities of computers may be used to process, continuously and simultaneously, all of the data which is inputted thereto. The parameters of the events, for example measurement and recognition of events or combinations which can constitute critical conditions, may be generated. In the third level, the information can be further analyzed so as to output data which identifies the parameters and conditions for observation or recognizes the particular critical parameters by comparisons with a data base of characteristics. Statistical sampling may occur, for example, as to how many events or defects are distributed in areas over certain size. Maps of the defects can be plotted. The third level may even use expert systems (artificial intelligence systems operating in accordance with human analogies) which characterizes the events and the source thereof in the process; for example, those defects, which arise out of operation of rollers, from dirt in hoppers, etc.

Accordingly, it is the principal object of the present invention to provide an improved system for the monitoring and analysis of continuous processes which involves the handling of enormous amounts of data so as to provide high resolution operation which is extremely sensitive to events and parameters of events of interest in the process.

It is a further object of the present invention to provide an improved system having a digital processing architecture which enable data such as necessary for the monitoring and analysis of continuous processes to be handled at very high data rates.

It is a still further object of the present invention to provide an improved system for the monitoring and analysis of continuous processes utilizing an improved digital processing architecture which enables data to be pipelined through sufficient parallel channels to distribute the processing along the data flow path so that different processes or the same process requiring a large number of computations and other operations can be carried on in parallel and concurrently.

Briefly described, a system for the monitoring and analysis of a continuous process in accordance with the invention makes use of sensor means responsive to the process for continuously generating signals. These signals are digitized to provide a continuous flow of first digital signals. Means are provided which are operative continuously and in parallel upon the first digital signals for reducing the first digital signals into a continuous flow of second digital signals occurring at a reduced rate from the rate of flow of the first digital signals. These second digital signals represent predetermined events in the process, such as critical parameters and defects in a web, when the process is the production of webs of high quality. Finally, means are provided which are responsive to and operative continuously upon the second digital signals for providing outputs representing the analysis of certain effects in the process represented by the events, for example outputs representing statistical quality control information as to the categories location and even the source of the events (e.g., the defects or imperfections in the web).

The foregoing and other features, objects and advantages of the invention, as well as a presently preferred embodiment thereof, will become more apparent from a reading of the following description in connection with the accompanying drawings in which.

FIGS. 8A-8M in the appendix hereto is a flow chart illustrating the programming of the second and third level defect analysis processors, the flow chart being broken up into several sections illustrated as FIGS. 8A-8M.

Figure 1:
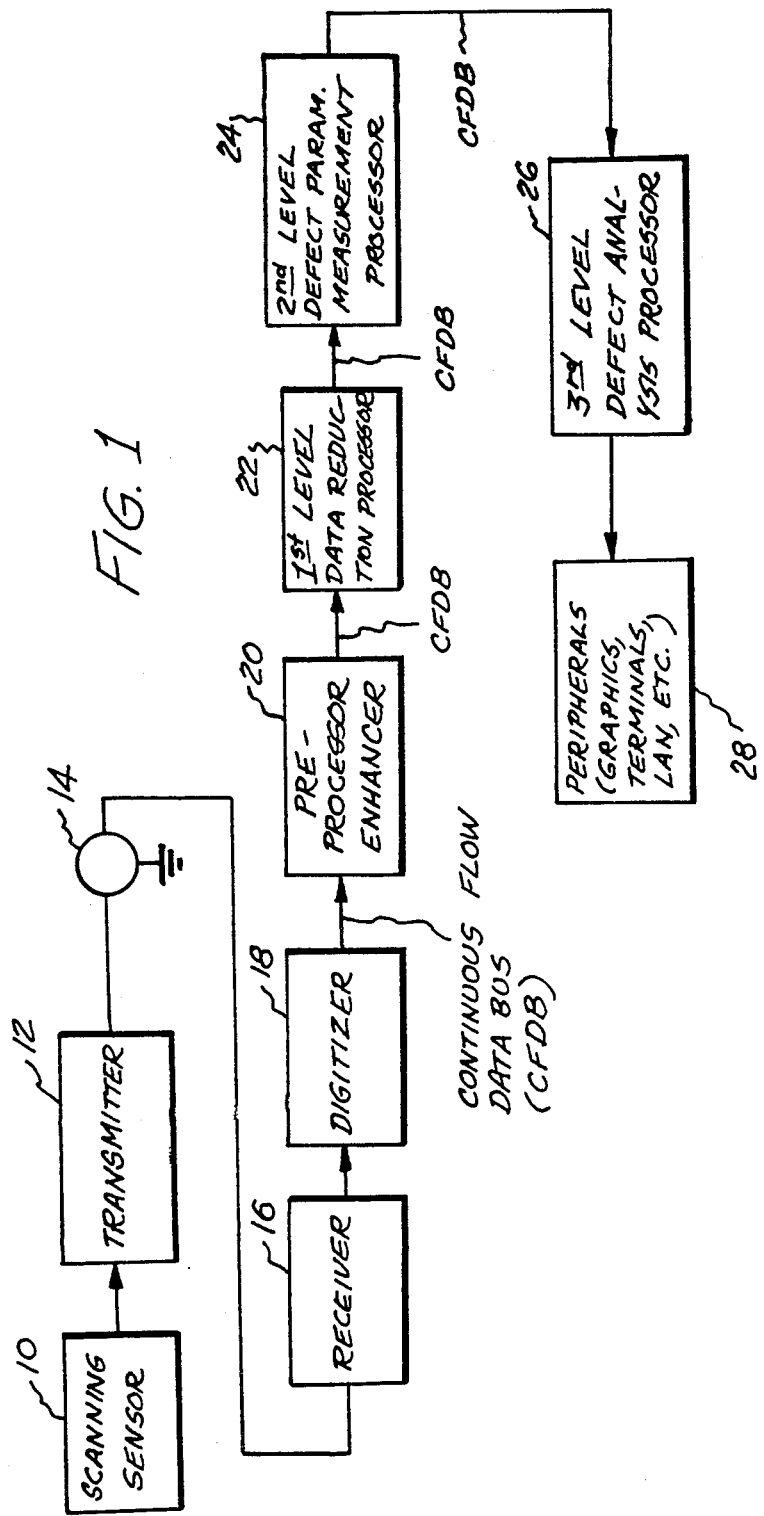
FIG. 1 is overall block diagram of a system for the monitoring and analysis of a process, which is provided in accordance with the invention.

Referring to FIG. 1 there's shown a system for monitoring and analysis of a process where a scanning sensor 10, such as a video camera, outputs signals continuously and at a sufficient rate to resolve parameters of the process. The process in a preferred embodiment of the invention is the production of webs which, for example, may be coated with material particles. The parameter may then be the density of the coating which may have defects in which the coating is different from the required density or absent, in areas varying from microscopic to macroscopic size. The output of the sensor may be an analog signal. A transmitter 12, which contains signal conditioning electronics, controls the amplitude level of the signals so as to facilitate the transmission thereof by way of a cable 14 to the portion of the system which digitizes, processes and analyzes the signals so as to monitor and analyze the process.

A receiver 16 at the output end of the cable 14 may also contain signal conditioning electronics so as to accommodate any losses or distortion during transmission. A digitizer 18 translates the signal into digital form. The digitizer may provide an output digital signal (e.g., a byte which contains 8 bits of data) corresponding to each pixel of consecutive pixels which are scanned and are closely spaced on web. The digitized signals may also represent other process parameters which occur at a rapid rate, for example of the order of ten million per second. The term "pixels" should be taken as comprehending successive measurements of a process parameter analogous to pixels from a web surface or other area which is scanned.

A continuous flow data bus (CFDB) which operates at a rate compatible with the digitized data, for example 12 megahertz (MHz) is used to carry the digital signals between various modules of the system. A suitable continuous flow data bus is the VME (Virtual Memory Eurobus). This bus may be a bidirectional bus. It is a feature of this invention to use multiple buses to link modules together, thereby eliminating the bottleneck of using one bus to transmit and receive data for each module. The bus has interfaces at the outputs and inputs of the modules which it interconnects. While the buses are shown connecting the modules in tandem, additional buses may be used to bypass modules, as where the function of a preceding module is handled in a succeeding module. The module which transfers the data can operate as a bus master so that the bus can transfer data from one module to several other modules or units on the same bus. The rate at which the input signals are digitized in the digitizer 18 is synchronous with the pixel output rate of the scanning sensor. The digitized signals from the digitizer may be inputted asynchronously to succeeding modules, under the control of the sending module (each module feeds the next) at the rate which the receiving module is capable of handling the data. The data rate of the succeeding modules may vary for short periods from the pixel rate. On average, the module's data rate handling capability should equal or be greater than the pixel rate.

For web monitoring and analysis, it is desirable to utilize a pre-processor 20 which enhances the characteristics of defects and reduces the effects of noise or unwanted effects in the scanned image. The pre-processor enhancer 20 provides enhanced digital signals, one for each pixel to another CFDB which transfers this data to a first level data reduction processor 22. This processor 22 encodes the data into signals for documented domain boundaries representing the defects; i.e., the signals are encoded so that the location thereof is contained in the reduced data. This is condensed or compressed data which represents the events of interest. These events, in the case of a web process, are the defects or imperfection characteristics and locations. The first level data reduction processor 22 may include several processors operating simultaneously and in parallel in order to handle data at a rate compatible with the input data rate.

The compressed data is transferred by way of another continuous flow data bus to a second level defect parameter measurement processor 24 where parameters of the event are computed. This processor may include one or more arrays of parallel computers which can handle successive groups of successive digital signals outputted by the first level processor 22. Measurements of the events in the case of a web process may be the widths, breadths, areas or other measurement of the defects, for examples holes within holes. These measurement processors can also be programmed to carry out convolution, Fourier transforms, thresholding, run length encoding, which may be allocated in whole or in part thereto instead of to the pre-processor enhancer 20 of the first level data reduction processor 22. Preferably the second level processor 24 handles the more complicated defect measurement functions of the system. The processors 22 and 24 perform their functions on a pipeline or systolic basis so as to be capable of handling the data rates involved.

Another CFDB outputs digital signals from the second level processor 24 to a third level defect analysis processor 26. This processor may be a host computer which controls the operation of other modules of the system, for example the pre-processor enhancer 20. The processor 26 may consist of one or more computers and co-processors, such as MC68020 micro-computers and MC68881 math co-processors which are available from Motorola Computer Products in Phoenix, Ariz., U.S. This processor 26 is interconnected with peripherals, such as disk memories which contain programs, graphic controllers and graphic terminals, display terminals, printers and plotters and also communication controllers for connecting local area networks (LANs) to the processor 26. The processor 26 may contain a multitasking operating system for performing various processes which provide analysis of the effects represented by the events obtained by the second level processor 24. These effects may be statistical characteristics of the events, categories of the events and reports with respect thereto which are displayed, communicated or printed out by the peripherals 28. A map of defects on the web may be created so as to allow the operators to remove low-quality portions of the web and verify that high-quality web material is being produced.

The defect analysis (third level) processor 26 may contain a pattern recognition program which categorizes the defects. An expert or artificial intelligence system may also be programmed in the third level processor. The events from the second level processor representing the characteristics of the imperfections may in the course of such an expert system program be compared with a data base which is created by a human operator. Categories of defects may be recognized in terms of differences between the characteristics and the data base characteristics. The categories may be related to the source of the defects, for example rollers or dirt in hoppers. More specifically, the third level processor 26 may be programmed to develop a logic table, for example of parameter lengths greater than certain lengths or areas of defects greater than certain areas in multiple fields of the table. The table is then accessed to compute the most probable differences which characterize the defects. A different table is then created and used to characterize the defects in real time. In addition to display and logging of defect characteristics and categories, the processor 26 may also provide data for controlling the web production process by automatically stopping the web to maintain the quality of the materials being produced.

Figure 2:
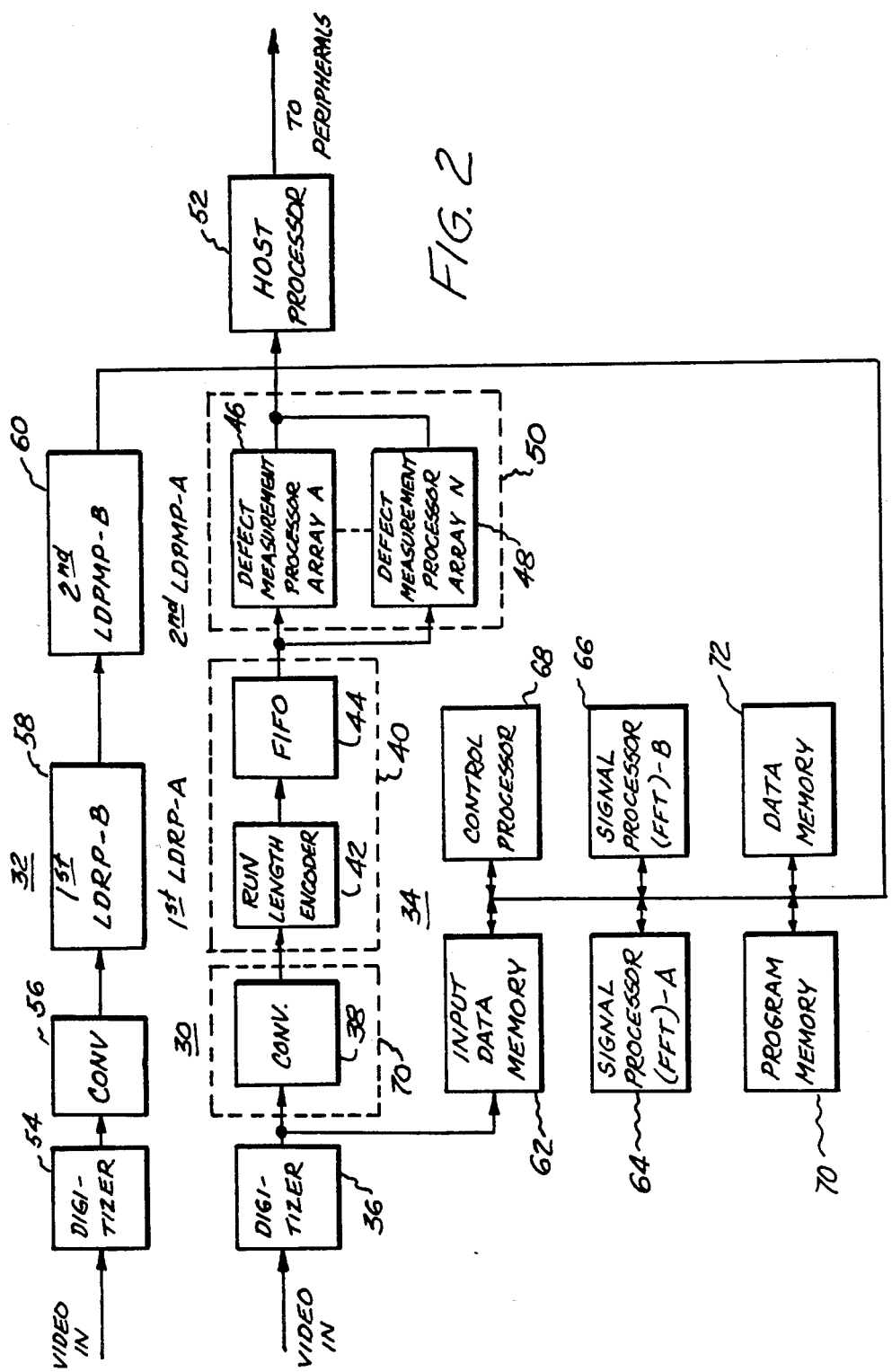
FIG. 2 is a more detailed block diagram illustrating the system shown in FIG. 1 which is particularly adapted for the analysis of defects in a web in an architecture utilizing a plurality of distributed processing channels which can operate concurrently upon signals resulting from the scanning of the web.

Referring to FIG. 2, there is shown a multichannel process monitoring and analysis system, which enables even more data to be handled than in a single channel system, or allows different processes to be performed simultaneously on the same data. The input data may be a video signal as from a scanning sensor. One of a plurality of processing channels 30 is illustrated in detail. Another channel 32 similar to the channel 30 is also illustrated. There may still be further parallel channels similar to channels 30 and 32. Three channels may be used for different primary colors. Another parallel channel 34 is provided for performing other measurement processes than are performed in the channels 30 and 32 and in parallel and simultaneously with the processing which is ongoing in the channels 30 and 32.

The channel 30 includes a digitizer 36 similar to the digitizer 10 (FIG. 1). A convolver 38 provides the function of the pre-processor enhancer 20. The first level data reduction processor 40 (1st LDRP-A) operates on the enhanced data from the convolver. The first level data reduction processor utilizes a run length encoder 42 which outputs digital numbers representing the occurrence and location of the events (e.g., defects in the web) to a first-in, first-out (FIFO) memory 44. This memory may store several thousand bytes, each of compressed data. This data is accessed on a round robin basis in successive data groups, in order of the arrival of the data in the FIFO, by one or more defect parameter measurement processor arrays. Two of these arrays 46 and 48, which represent the first (A) and the Nth array, are shown. Each array may contain a plurality of, preferably four computers. An enormous amount of data is processed simultaneously and in parallel by the N arrays. These arrays provide the second level defect parameter measurement processor 50 (2nd LDPMP-A). The process parameters computed by the 2nd LDPMP-A 50 are transferred to a host processor 52 which provides the third level defect analysis processor function. The host processor is connected to peripherals such as the peripherals 28 discussed above in connection with FIG. 1. All of the modules are interconnected by continuous flow data buses, such as VME buses.

The parallel channel 32 similarly has a second video input and includes a digitizer 54, a convolver 56, a first level data reduction processor 58, (1st LDRP-B), and another second level (2nd LDPMP-B) 60. The latter processor 60 is connected to the host-processor 52. The processor 60 may include one or more defect measurement processor arrays. Each of the channels may, for example, be operated using separate sensors or via a multiplexer for handling successive side-by-side strips of the web. Alternatively, the 2nd LDPMP-B may be programmed to provide a measurement of different characteristics than the 2nd LDPMP-A 50 of the first channel 30. The host processor accesses data from the various processes in the array in order to compute the effects (e.g., categories of defects having different characteristics) which are represented by the data from the various processors of the channels 30 and 32.

The channel 34 constitutes an intelligent filter unit. The same data that is provided by the digitizer 36 to the convolver 38 is applied to an input data memory 62. This may be a FIFO memory which stores data from a plurality of scans, say eight successive scans. This data may be inputted at the same data rate, for example 10 to 20 megabytes per second. The channel 34 includes two signal processors 64 and 66 which are connected by way of a databus to the memory 62, a control processor 68, a program memory 70 and a data memory 72. The signal processors 64 and 66 are identified as FFT-A and FFT-B. These may be commercially available computer chips which are programmed by program data in the program memory under the control of the control processor 68 to perform fast Fourier transforms of different types of the same type in parallel so as to calculate and provide digital signals as to the frequencies in the scanned video signal, as for texture analysis measurements. The control processor 68 may also be a commercial signal processing chip such as the Texas Instruments TI 32020, which accesses data byte-by-byte from the memory 62 and transfers it to the data memory 72, which may be a random access memory (RAM).

The signal processors 64 and 66 perform a fast Fourier transform analysis on one or more lines of data. The results of this analysis are digital signals provided to the host processor 52. The host processor is programmed in one of its tasks to compare the data with data in its database representing different spectra. The outputs may be used to display defects or to provide signals for process control purposes. So as to have information respecting the location of the defects represented by the FFT data, synchronizing signals may be provided to the host processor from the digitizer, either directly or by counting the transfers of bytes from the input data memory 62 to the RAM 72. All of the data going to the channel 34 and in the other channels is coordinated by start of scan information generated by the sensor 10 (FIG. 1) as will become more apparent as the description proceeds.

The system is very flexible in allowing the selection of different measurement processes all of which run in real time in sufficient channels to handle the input data rates and the billions of computations necessary to obtain the parameter measurements.

Figure 3:
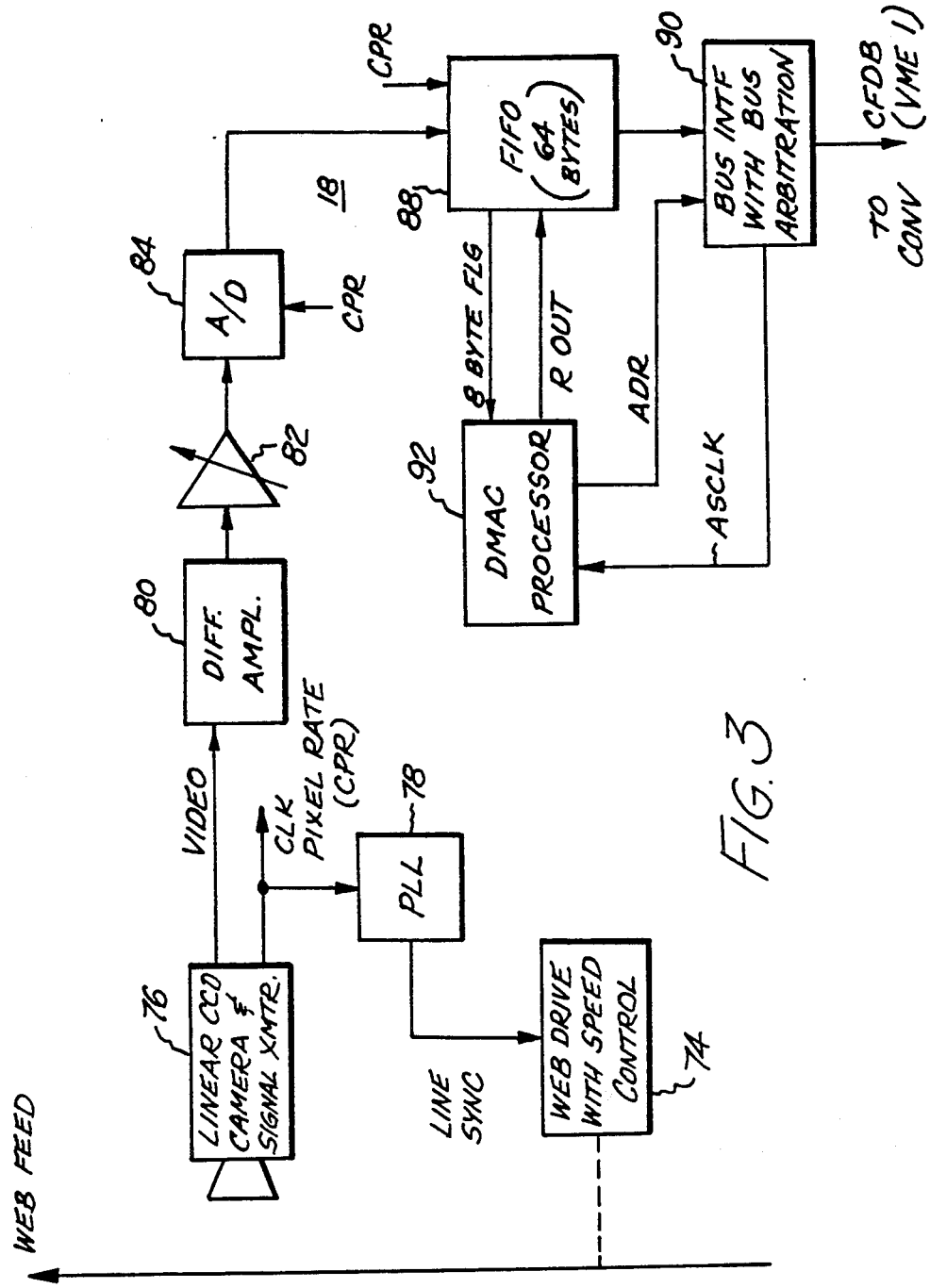
FIG. 3 is more detailed block diagram of digitizer suitable for use in the system shown in FIGS. 1 and 2.

FIG. 3 illustrates the sensor with its transmitter and the receiver 16 and the digitizer 18 in greater detail, as applied to a web production process. The web is fed by a web drive with a speed control or controller circuit 74 at a nominal rate, for example 300 meters per minute. The web may be approximately from a few centimeters to meters wide. The web is scanned by a linear CCD (charge couple device) video camera 76. This camera may be equipped with a signal transmitter which is located in or very near the camera 76. The transmitter electronics changes the level of the signal and transforms into a signal which has higher noise immunity for transmission, for example via a coaxial cable to the other circuits of the system. The camera may have a pixel resolution of 2K (2,048) pixels per scan line. In other words, there may be 2,048 CCD elements, each of which provides a successive analog signal which is clocked out of the camera as the video signal together with a clock at the pixel rate (CPR). This clock locks a phase-lock loop 78 which produces synchronizing signals at the line rate. These line-rate sync signals are transmitted to the web encoder interface and may be used to control web speed so that the scan lines are equally spaced.

The receiver 16 at the output of the cable may include a differential amplifier 80 which is adapted to handle a balanced pair of leads in the cable and is isolated from ground. The output of the differential amplifier is connected by way of a variable gain amplifier 82 to an analog to digital (A/D) converter 84. This converter may be a flash type A/D which is operated at the pixel rate by the CPR clock. The gain of the signals is adjusted as with the amplifier 82 so that the darkest level and the lightest level are represented by digital signals of lowest and highest value (0 to $2^7$) for each 8 bit byte which is outputted by the A/D. At nominal brightness the output code has a value of $2^4$.

The output bytes are buffered in a FIFO memory 88 (a shift register) which is clocked at the CPR rate which has capacity for a group of bytes; sixty-four capacity bytes being suitable. Data is transferred to the continuous data flow bus indicated as CFDB (VME 1) by a bus interface 90 which has bus arbitration logic. The transfer of data is controlled by Direct Memory Access (DMAC) processor 92.

Figure 4:
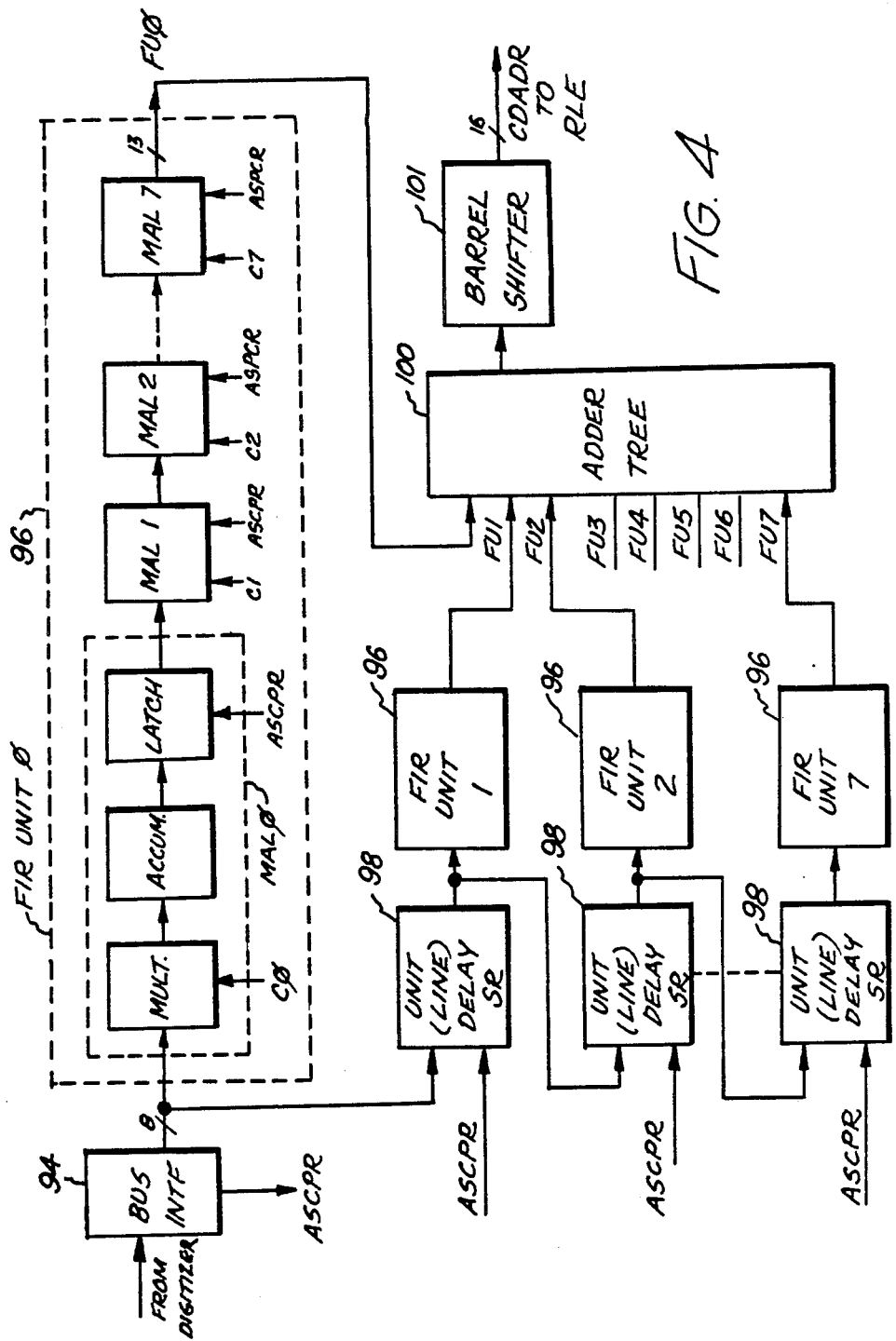
FIG. 4 is more detailed block diagram of a pre-processor enhancer (convolver) which may be used in the system shown in FIGS. 1 and 2.

In operation, as the FIFO 88 fills up, the DMAC processor 92 detects when 32 bytes have been stored in the FIFO 88. The address of the byte in the FIFO to be read out is applied to the bus interface. The bus arbitration logic tests the bus to see if it is available to take data and to transfer that data to the convolver (38 in FIG. 2). The DMAC is the bus master. Bus transfer and interface 90 operations are detailed in the applicable bus specification promulgated by the Institute of Electrical and Electronic Engineers (IEEE). Briefly, if the convolver is available to take data, a line on the bus will be at the appropriate level. Then an asynchronous clock (ASCLK) pulse is generated in the bus interface 90 and applied to the DMAC 92. A read out pulse (ROUT) is then applied to the FIFO and data is transferred to the bus. After the data is transmitted, an acknowledge signal indicating the address of the data is transmitted back from the convolver bus interface 94 (FIG. 4) which enables the next ASCLK pulse to be generated. Then the bus is available for the next byte. The ASCLK rate is a function of how fast the DMAC 92 can output data and how fast the bus can receive the data. One byte is transmitted at a time. The bus 16 may be 16 bits wide and is capable of outputting all bytes on the low byte or high byte sides of the bus. By using both the low and high byte sides (each eight bits wide), the data transfer rate can be doubled. The rate is determined by how fast the convolver can handle the data. The VME bus may transfer data at a 20 to 40 megabyte rate. The convolver, which is described in detail here and after in FIG. 4, is capable of handling data at a pipeline rate faster than the digitization rate. Therefore, it will be apparent that the digitizer including the A/D 84, the FIFO 88 and the DMAC 92 is capable of digitizing data and transferring it to the remainder of the system at a rate compatible with any practically achievable digitization rate for high resolution. It will be appreciated that 2048 pixels per scan line represents a high-resolution system. The system may be operated at still higher resolution, for example 4096 or 8192 pixels per scan. Lower resolutions may be used, for example 512 or 1024 pixels per scan, if desired.

The digitizer and the other modules of the system may be arranged on circuit boards which connect into a back-plane circuit board containing the VME buses. Each board has connections to two or more buses so that data may flow into the board on one bus and out on another bus. The buses may be very short in length as to tightly couple the modules and facilitate the handling of the digital signals at data rates of the order of tens of megabytes (e.g., 20–40) per second.

Referring to FIG. 4, there is shown a convolver operative in a pipeline manner to provide for the handling of the digitized data at the high-data rates which are used in the system. The convolver utilizes the bus interface 94. Upon receipt of each byte, the convolver outputs an asynchronous pixel rate clock (ASCPR). Each ASCPR pulse corresponds to each byte. There are a predetermined number of pixels per scan line (2048 in the exemplary system discussed herein). Since each byte corresponds to a successive pixel, the number of ASCPRs corresponds to the location of the pixel. The convolver is made up of a plurality of finite impulse response (FIR) units which are operative simultaneously and in parallel. In the exemplary system described herein, there are eight FIR units 96. These are identified as FIR unit 0, FIR unit 1, FIR unit 2, . . . FIR unit 7. Each FIR unit provides a separate multibit output signal 13 bits wide. These signals are designated FU 0, FU 1, FU 2, . . . FU 7.

Figure 6:
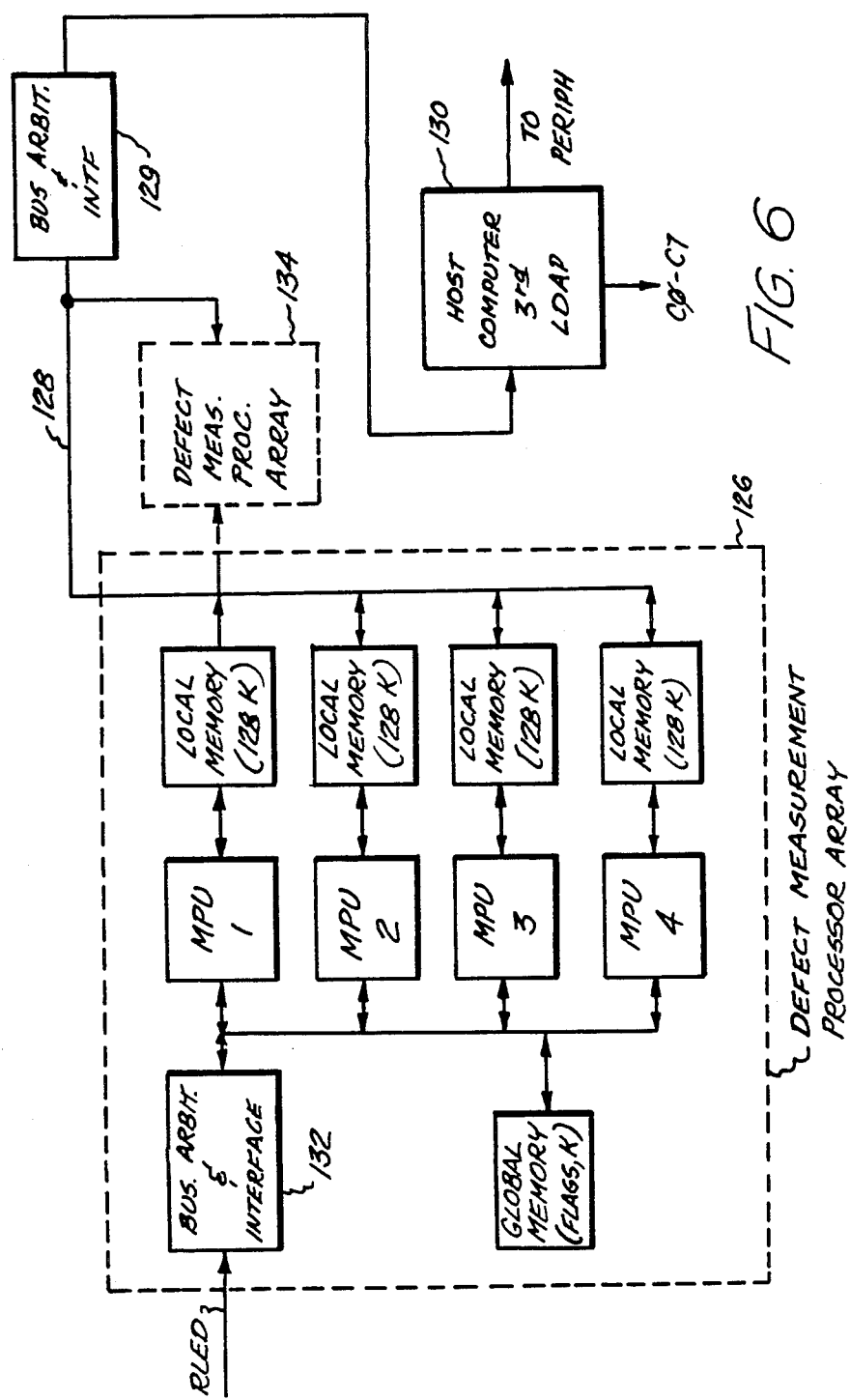
FIG. 6 is a block diagram of a second level defect parameter measurement processor which also shows a host computer as the third level defect analysis processor, both processors being illustrated in FIGS. 1 and 2.

The FIR units each contain a plurality (eight in this example) of multiplier, accumulator and latch elements which are connected in tandem. These elements, in the case of the FIR unit 0, are identified as MAL 0, MAL 1, MAL 2, . . . MAL 7. The multipliers multiply the input bytes thereto, which in the case of the first multiplier comes from the bus interface 92 and for the successive multipliers from the latches of their preceding MAL units, with co-efficients C0, C1, C2, . . . C7. These co-efficients are generated in the host computer which forms the third level defect analysis processor (3rd LDAP), as is shown in FIG. 6.

Each FIR unit corresponds to a successive scan line. By the use of unit (line) delay shift registers (SR) 98 which are connected in a pipeline to the bus interface 94 pixel bytes from successive lines are applied to the different FIR units 96. By using eight SR and eight FIR units, a kernel of eight by eight pixels may be used. The kernels may be extended in length by increasing the length of the unit delay. For example, by doubling the unit delay to 4096, pixels from alternate successive lines are inputted to the different FIR units 96. The kernel size can, therefore, be changed. By utilizing fewer or more than eight MAL units, the width of the kernel can be reduced or increased.

The FIR units are basically shift registers whose elements are multiplier accumulators and latches. Such FIR units are commercially available which are capable of handling four bit bytes. Two such four bit FIR units may be arranged in parallel to provide the eight-bit byte FIR units shown in FIG. 4.

Operation of the FIR units provide composite running sums of products of each pixel byte with the co-efficients. These running sums are represented by the 13 bit digital signals FU 0 through FU 7 at the output latches of the last (MAL 7) elements of the FIR units 96. These data are applied to an adder tree 100 which adds the running sums to provide an output corresponding to the convolution of each kernel. The additional process may produce a seventeen to twenty-four bit number. A barrel shifter 101 allows the sixteen bits which most effectively denote the defect (the CDADR signals) to be outputted.

Figure 5:
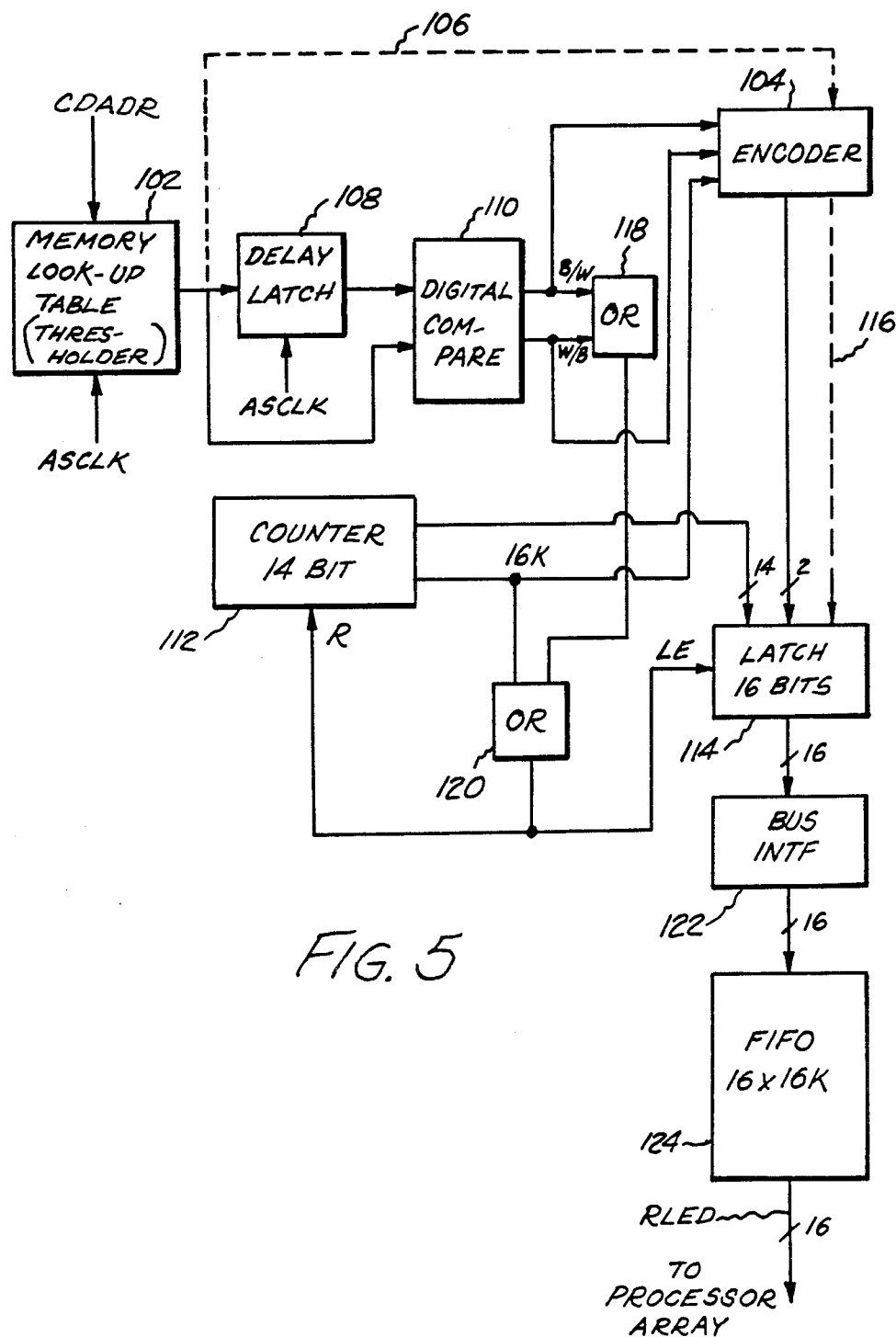
FIG. 5 is a block diagram of a first level data reduction processor, specifically the run length encoder and FIFO memory illustrated in FIG. 2.

These 16 bit digital signals (CDADR) are inputted by way of the next VME bus to the run length encoder, which is shown in detail in FIG. 5. There a memory having a look-up table or thresholder 102 transforms at the full multi-megabyte data rate, the CDADR data from the convolver. The look-up table in the memory provides a threshold function and can output a single bit to indicate a defect event. The bit is a "1" for an area which is above the threshold. This area may be deemed a white area. A zero bit is provided for an area which is below the threshold (black). A transition from white to black or from black to white indicates a defect. The table may be in accordance with a linear function with all CDADRs values below a certain level deemed black and those above that level deemed white or it may be nonlinear (e.g., a log or exponential function). The function may be continuous or discontinuous. The table may permit thresholding to several levels which may be represented by a multibit output signal. In other words, the look-up table memory 102 may provide a multibit output. The memory 102 may be loaded to provide different outputs for each value of the 16 bits CDADR input. Therefore, there is a great deal of flexibility in recognizing a defect. In the simplest and presently preferred case, only a single-bit output representing a black or white pixel from the enhanced pixel data provided by the convolver is outputted by the memory 102.

If a multibit output is used, the bits may be directly passed to an encoder 104 as indicated by the dash line 106. A delay latch 108 provides a one-bit delay as determined by the ASCLK which operates the latch so as to provide successive outputs from the memory 102 to a digital comparator 110. This comparator indicates when there is a change between successive outputs of memory 102. For example, the comparator provides two outputs depending upon whether the inputs are "1" "0" or "0" "1". One of these outputs, therefore, indicates a black to white (B/W) transition while the other represents a white to black (W/B) transition. Outputs from memory 102 or these B/W and W/B bits are presented to the encoder 104 which also receives an output from a counter 112 which counts the ASCLK pulses. It will be recalled that the ASCLK pulses arrive with the pixel data and contain location information. When the counter rolls over or reaches 16K (the counter being 14 bit ($2^{14}$) counter), an output is also provided to the encoder. The encoder translates the outputs from memory 102 (e.g., the 3 bits presented to it) into a 2-bit signal in the highest order bits of a 16-bit signal (14 bits coming from the counter 112) to a 16-bit latch 114. In the event that the thresholder memory 102 provides a multibit output, additional bits indicating the nature of the characteristic of the defect may also be applied to the latch as indicated by the dash line 116.

When the comparator indicates a change in memory 102's output (e.g., B/W or W/B transition), that event is flagged via an OR gate 118 and another OR function gate 120 to reset the counter 112 and provide a latch enable (LE) signal to the latch 114. The OR function 120 also receives an input when the counter rolls over which occurs when 16K or eight lines of pixel at the 2048 pixel per line rate occur without a defect transition being detected. Accordingly, the latch will have data in it indicating the number of pixels between transitions and the occurrence of eight lines from the last transition.

This data is accessed by another bus interface 122 to a FIFO memory having capacity for 16K of encoded data. This data is run length encoded data (RLED). This data is accessed by the processor array in the second level defect measurement processor. The FIFO memory 124 serves as a temporary buffer and acts as a temporary overflow for times when a burst of defects may occur. The second port of the FIFO memory 124 is connected by way of another continuous flow (VME) data bus to the defect measurement processor array shown in FIG. 6. This array 126 may be referred to as a quad array since it contains four microprocessor units MPU 1, MPU 2, MPU 3, and MPU 4. Each of these units is suitably a 16-bit microprocessor such as the Motorola MC 68010. To be compatible with the data rate, each of these computers can be run at a rate of 12 MHz with no wait states. Each of the MPUs has a local memory which has suitably 128K (128 kilobytes) capacity. A data bus connects the input ports of the MPUs to a local bus. This bus is connected to a global memory which contains flags and constants. The flags may be used to denote the location with respect to the web (where in the course of each scan and during which of the scans from the start of scan or initialization of the system) is the end of the domain for which each MPU is responsible for performing computations. Each MPU, because of its own local memory which can contain program data, runs independently so that parallel, concurrent processing will be carried out on the RLED data. Each of the local memories can be programmed through a bus 128 by the host computer 130. The host computer also provides the third level defect analysis processes. It is connected to the peripherals and also provides the co-efficients, C0 through C7 for the convolver.

The RLED data is selected by each MPU which acts as bus master through a bus arbitration and interface unit 132. Each MPU takes RLED data successively on a round robin basis (viz., MPU1, MPU2, MPU3, MPU4, MPU1, MPU2 . . . ). For example, each MPU takes sixty-four bytes of RLED data and performs the measurement or other process which it is programmed to perform. The MPUs operate concurrently on successive sixty-four byte groups of data which are extracted from the FIFO 124 (FIG. 5) through the bus and via the bus arbitration interface 132.

The RLED data, as discussed above, contains information as to the location of each defect transition. For example, the first RLED code may be a count equal to 800 pixels in from the beginning of the first scan (initialization of the system). There may be another transition 10 counts higher to indicate the end of a defect area. Still later, there may be a roll-over or 16K code to indicate that there have been no defects for eight scans. Thus, the MPUs can readily, and without burdening the computation process, keep track of the location of each occurrence of a defect. The flags in the global memory keep track of where, with respect to the web, each MPU has completed its computations and the next MPU has begun its computations.

Not only can programs be loaded into the local MPU's memories from the host computer 130, which loading can be mapped by utilizing fixed windows of time on the host to local memory bus 128, the MPUs can also interrupt the host computer 130 to relay the status on any results which may have been calculated.

The host computer bus arbitration and interface 129 is shown connected in a parallel path to the bus 128 to an optional successive defect measurement array 134. This array is shown in dash lines in order to indicate its use is optional. The array 134 may be similar to the array 126. It may be programmed to operate on the results of the computations in the first array 126, when further and additional computations are necessary in order to provide measurement results in real time. As discussed in connection with FIG. 2, there may be still further arrays connected in parallel with array 126. The system is flexible and allows as many series or parallel defect measurement arrays as are necessary to provide the computations desired. The use of the continuous data buses which enable any array or MPU in an array to become bus master provides flexibility in selection of the sequence and extent of data on which each MPU in any array can perform the required calculations.

Figure 7:
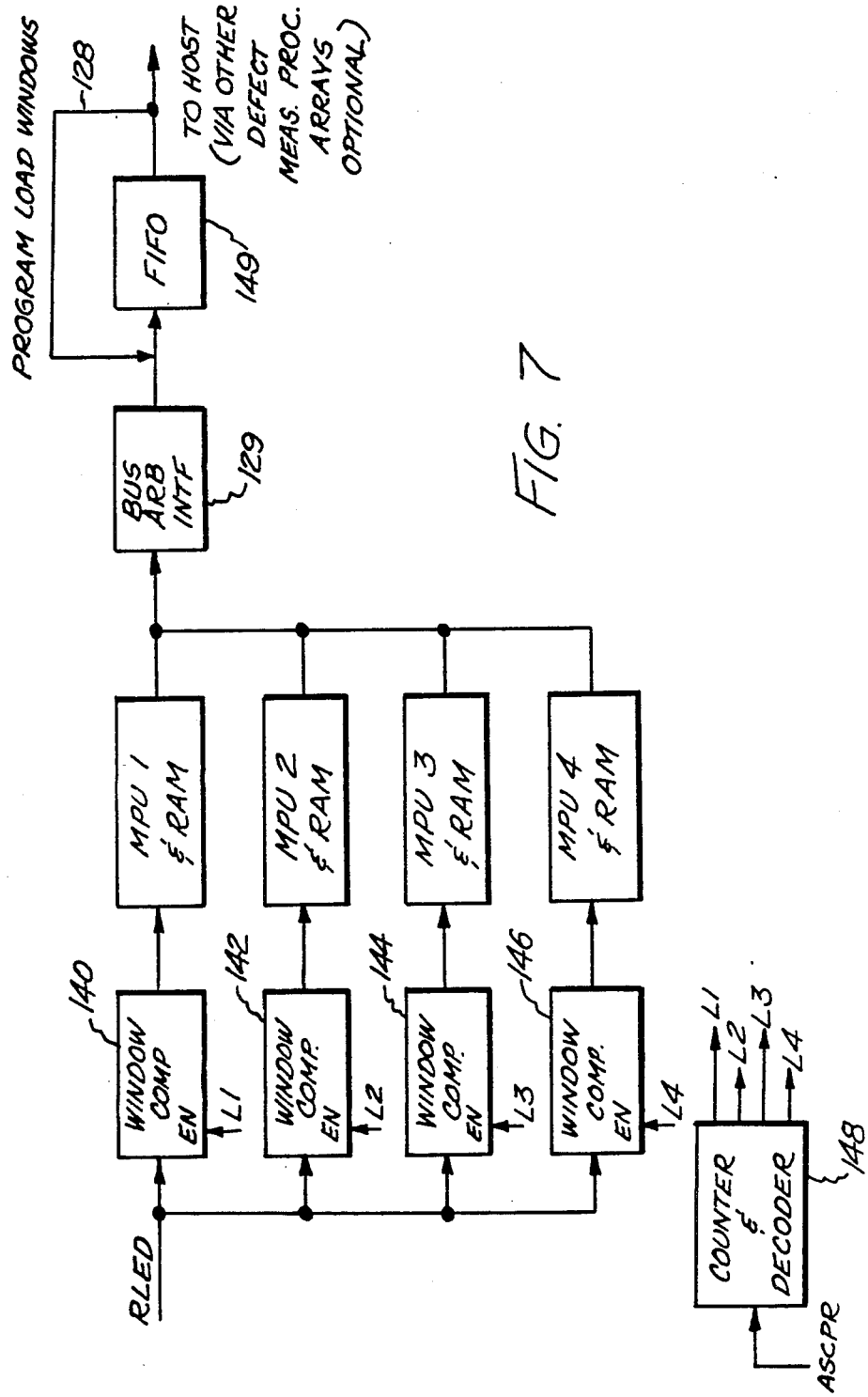
FIG. 7 is a block diagram illustrating another embodiment of the first level defect parameter measurement processor.

If defects occur at a rate faster than computations on RLED data can be performed, the FIFO memory 124 (FIG. 5) will become overloaded and an alarm will be indicated. In most systems such an alarm will be sufficient since, the web quality would necessarily be below predetermined standards. There are certain cases where the web may provide an extremely large number of transitions (RLED data bytes). These may be referred to as busy scenes. To enable computations to be performed without overloading a buffer such as the FIFO, the RLED data may be provided directly from the bus interface 122 (FIG. 5) to window comparator units 140, 142, 144, and 146 which are associated with different ones of the quad MPUs and their local (RAM) memories. See FIG. 7. These MPUs and RAMs may be similar to the MPU 1, 2, 3 and 4 and local memories shown in FIG. 6.

In order to enable each comparator to operate on a successive group of RLED data, the pixel count information is encoded into addresses by a counter and decoder 148. These addresses indicated as L1, L2, L3, and L4 may each cover approximately eight scans successively along the direction of travel of the web. Preferably, however the addresses may be variables with decoding set by the host depending upon the number of defects being detected. In operation each MPU will then receive such RLED codes as are produced in a successive group of scans. The MPUs then perform processes on successive groups of RLED bytes. The count range for each scan may be adjusted depending upon how busy the scene happens to be. Such adjustment can be made by the host computer. The host computer may also receive the calculation result information through the bus arbitration and interface 129 and a separate buffer storage FIFO unit 149.

Referring to FIGS. 8A to 8M in the appendix, there is shown a typical program for performing measurements on RLED data. These FIGS. are discussed in the appendix.

From the foregoing description, it will be apparent that there has been provided an improved system for monitoring and analysis of continuous processes. While the system has been described in detail in connection with a web production quality control process, the invention is applicable generally to process monitoring and analysis and even the control of the process which is monitored. Accordingly, variations and modifications within the scope of the invention will certainly become apparent for such other applications and also for the enhancement of the monitoring, analysis and control of a web production process. Accordingly, the foregoing description should be taken as illustrative and not in a limiting sense.

APPENDIX

FIGS. 8A–M show the programming of the array 126 which contains the four or Quad MPUs or coprocessors and is referred to as the Quad Board Coprocessor Measurement program. This program involves the programming of the host computer 130 (HOST) and covers the second and third level processing.

Figures 8A, 8B:
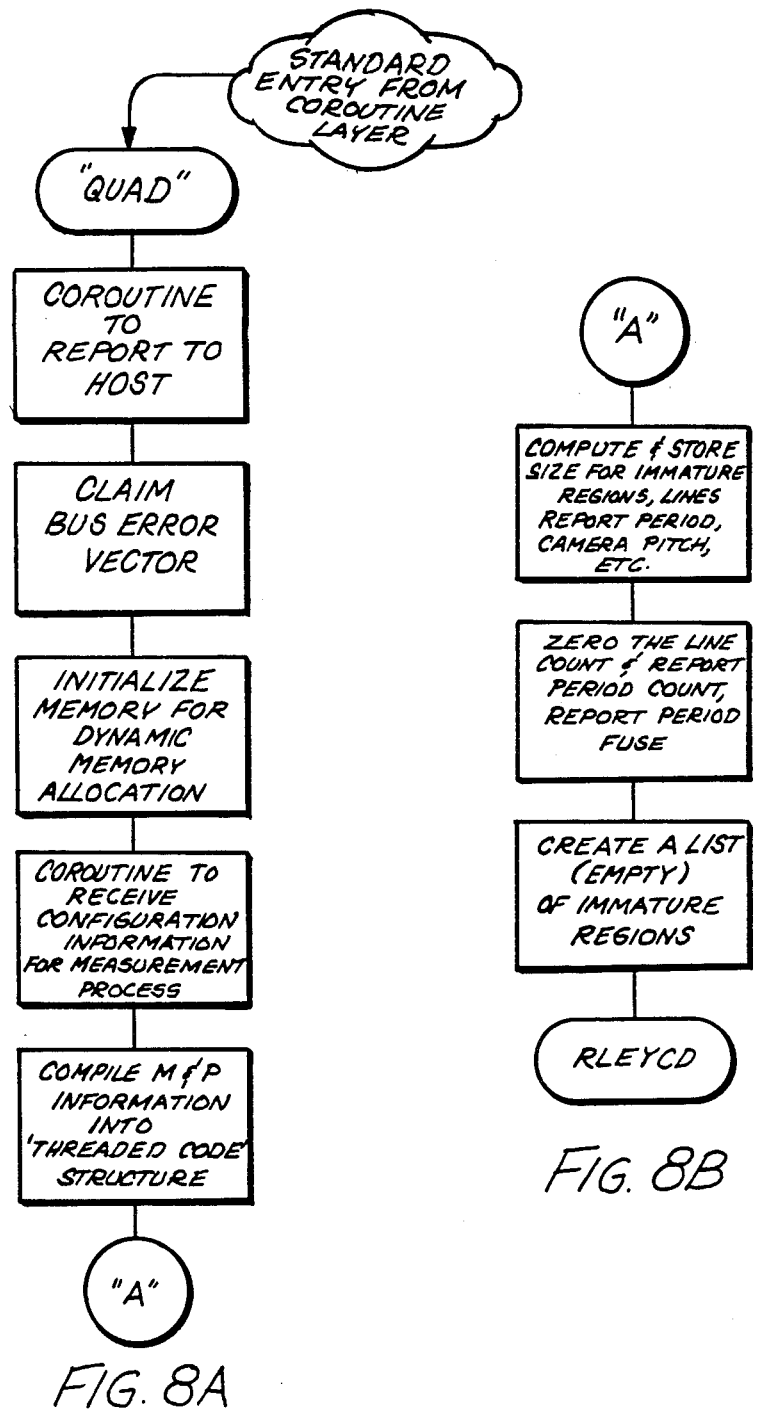

As shown on FIG. 8A, entry to the flowchart is made from a "cloud" and identified as an entry from the coroutine layer. For purposes of understanding the Quad Board Coprocessor Measurement, one can view the coroutine layer as playing the role of an executive or an operating system in its relationship to that portion of the instructions comprising the QBCMP (Quad Board Coprocessor Measurement Program). This is true in the sense that certain information comes to exist through the offices of the coroutine layer or that from time to time the QBCMP accomplishes its purpose by transferring control (in a programming sense) to the coroutine layer, and in doing so enables the transfer of the information which was its purpose to compute, to another (unspecified) computing entity.

The flowchart ellipse labeled "QUAD" identifies a terminus of the QBCMP.

The first operation performed is to coroutine to report to HOST. This allows HOST to place information in the memory of the QBCMP which will partially determine parameters of the program. Parameters which are placed in memory by the HOST include the mask parameters, camera pitch, number of lines per report period, measurement calibration factors and any other constants used by the program.

The QBCMP proceeds by claiming the bus error vector by setting the bus error vector to its own routine. In this program, bus error is treated as a "normal" exception which occurs when an attempt is made to read later from the FIFO BOARD (including the FIFO 124-FIG. 5) while the FIFO BOARD is empty (has no data). When such an exception occurs, the program responds by recurring the instruction executing at the time of the exception. This permits data to be transferred from a FIFO which does contain data without any "overhead".

The QBCMP proceeds to INITIALIZE MEMORY FOR DYNAMIC MEMORY ALLOCATION. This refers to setting a value to memory which is unused for any other purpose and part of which is allocated to any computing entity within the QBCMP by calling an appropriate procedure.

The QBCMP perform a COROUTINE TO RECEIVE CONFIGURATION FOR MEASUREMENT (AND) PROCESS. This collection of information, received in the memory of the QBCMP program describes a way in which programs and data are to be interconnected and which, taken all together form a statement of what the QBCMP program is to accomplish.

The next step is to COMPILE M&P INFORMATION INTO "THREADED CODE" STRUCTURES. This step refers to taking the data comprising the contextual statement of what the QBCMP is to accomplish and re-casting that statement into a new form of data abstraction, given the term "threaded code", which has the property that is in an efficious form in which the actual purpose may be accomplished in coordination with actual data assembled as parameters by the invariant connectivity analysis portion of the QBCMP program (see process on FIG. 8H) and the compiled, threaded code portion which is brought into play by the various Executers. Executers will be described below.

As shown in FIG. 8B, on the next step: COMPUTE & STORE SIZE FOR IMMATURE REGIONS, LINES, REPORT PERIOD, CAMERA PITCH, ETC. Some of the constants used by the program can be computed only after the compilation steps which have just been completed. These constants are computed and stored at this time.

In the next step: ZERO THE LINE COUNT & REPORT PERIOD COUNT REPORT PERIOD RUSE, these variables are reset prior to starting the operation of the remainder of the program. The line count is zeroed at each repeat period. The portion of a report period establishes a way in which the measurement or an aggregate of measurements can make a statement about a stable quality of image extent.

The next step: CREATE A LIST (EMPTY) OF IMMATURE REGIONS establishes that the history of the scanned image prior to receiving any data from the input is totally background, or empty.

The last of the items on FIG. 8B is a transfer of control to instructions which are given the aggregate label RLEYCD. This is an acronym for Run Length Encoded to y-group coded data. Run length encoded data is an encoding of the pixels in an image by encoding the length of a run in bits 0 through 13, and the identity of the kind of pixel in the run in bits 14 and 15. This type of image encoding is converted to y-group codes in which the distance from the left border of each leading edge of similar kinds of pixels is encoded as each item of data. Following the leading edge of the last run of pixels in each line a "new line" code is entered in the succession of data. This "new line" code, in addition to starting a new line, can represent up to 32766 empty lines which might follow the last run of pixels. In addition to encoding pixels, new lines, and empty lines, error conditions are also encoded. This provides a simple way in which data can be processed concurrently by all coprocessors up to the point where the error condition occurred. RLEYCD is repeated in FIG. 8C.

In FIG. 8C, SYNCHRONIZE USING RAM SHARED AMONG COPROCESSORS refers to a synchronizing operation which allows the four microprocessors (micros) located on the board to divide the flow of input data. The reading and processing of the input data proceeds in round robin fashion with processing in three of the micros overlapping (in time) the reading and processing of the fourth microprocessor.

Next: ESTABLISH BUFFER SIZE (FROM HOST) OR DEFAULT results in the RLEYCD portion of the QBCMP determining how much data will be placed in the buffer containing y-group codes.

Next in SAVE ROOM IN BUFFER FOR DATA-FLOW EXCEPTION codes, the buffer size is adjusted to insure that sufficient room remains at the end of the buffer so that in the event an exception occurs near the end of the buffer, sufficient memory will remain in the buffer to encode the exceptions.

Next in INITIALIZE FROM THE SHARED RAM VARIABLES, because of the round-robin operation involving four microprocessors, a y-group code buffer will, generally result in Run Length encoded data which will overrun the last line which is placed in the y-group code buffer. This "fractured code" and the line count at which it occurs is placed in the shared RAM where the next microprocessor can use it to adjust its internal representation of location in the image approximately.

Next in the READ LOOP (FIG. 8D) the code from either the shared RAM or from the input data obtained from the FIFO is tested for background or figure. Depending on whether the run of pixels is background or figure and the current kind of pixel in the y-group code run, the appropriate y-group codes are computed. This continuous, looping through the Read Loop occurs as when an RLE code is emptied into the y-group code and continues until the y-group code buffer is filled.

It is important to note that the operation of synchronizing via the shared RAM, and processing the y-group codes and input RLE-codes (FIGS. 8E–G) results in filling the y-group code buffer at a rate much faster than the remaining processing y-group codes; provided of course that data is always present in the FIFO. This means that when "peak demand" occurs, the FIFO is emptied quickly and processing can run concurrently on all four microprocessors.

Following the filling of the y-group code buffer, the "baton is passed" to the next microprocessor in the round-robin cycle, and the program begins to process the y-group codes (YGC). See Process in FIG. 8H.

Referring to the flowcharts FIGS. 8H–M in overview, consider that three things are going on. These three things are closely related, but can be understood more easily taken one at a time rather than in chronological fashion. These things are connectivity analysis, basic measurement, and measurement process.

Connectivity analysis involves taking the y-group codes as input, and maintaining the list of immature regions in an appropriate "state" as a result.

Basic measurement involves performing a calculation which results in an incremental geometric statement, given the new horizontal run of pixels which is applicable to an immature region. This incremented geometric statement is associated with the appropriate immature region by keeping the data adjacent to the connectivity analysis data of the immature region. An immature region becomes mature in the program at 'LPT' when it has no fork relation. When this occurs, the incremental basic measurement is elaborated so that the data has the same form as measurement process data. Measurement process is a mechanism which provides for concepts involving devised measurements or other operations, including forming statistical summaries.

The foregoing will become further apparent from the following discussion.

In the operation of the system as discussed in the foregoing specification, there is early processing of an image consisting of Offset and Gain Correction, FIR processing, Thresholding and Coding. Once these steps have been performed, the coded image is 'infix' to the QBCMP program. This program creates and maintains data (called immature regions). This process embodies connectivity analysis. As the connectivity analysis is performed, opportunities for incremental measurement arise. The opportunities which arise are of five kinds:
1. At the first code of an upward projection
2. After the last code of a downward projection
3. At a code where two upward projections merge
4. At a code where two downward projections fork
5. At a code where a left and right edge exists Other processing may be associated with connected regions. In particular is the processing which occurs when the last code of a connected region has been processed. At that point, the immature region becomes mature. Further processing may now be required. This opportunity for processing is called End of Region Processing.

Now, if some processing, for example the end of feature processing, uses some Process RAM as a buffer, then this buffer may become full before some other processing is ordained to download the buffer contents. This spells out another time when some processing may be required.

Figure 8H:
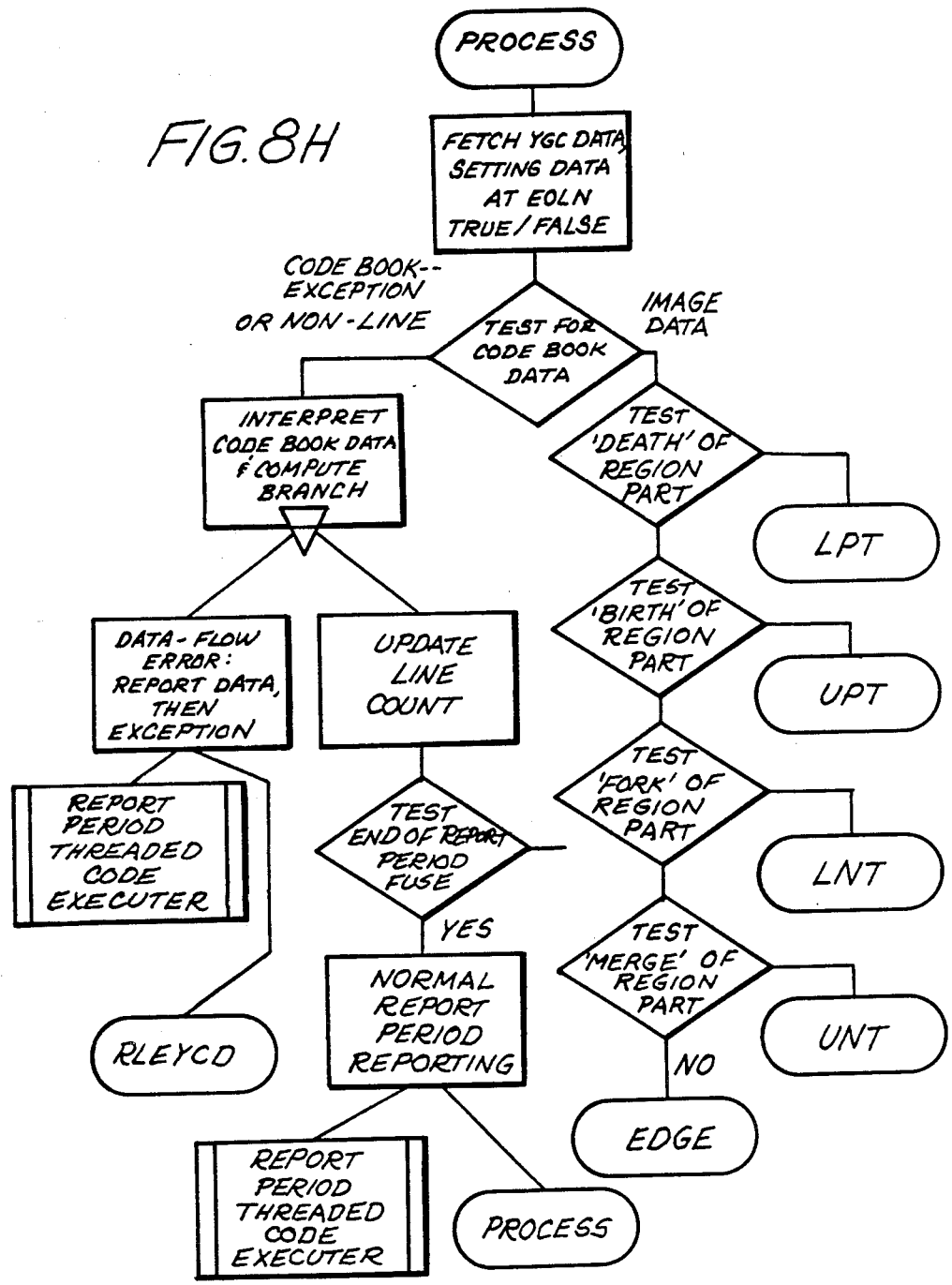
Figure 8I:
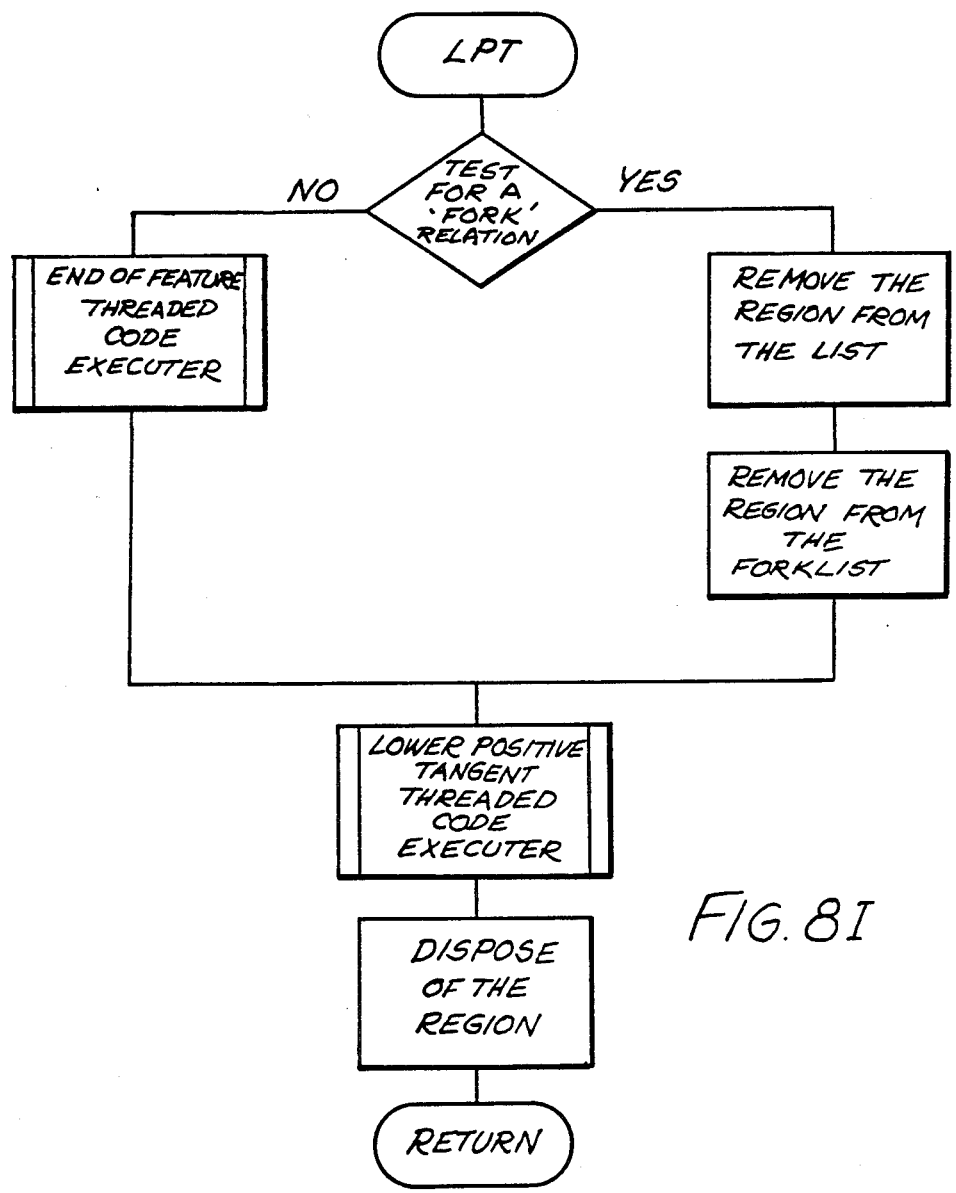
Figures 8J, 8K:
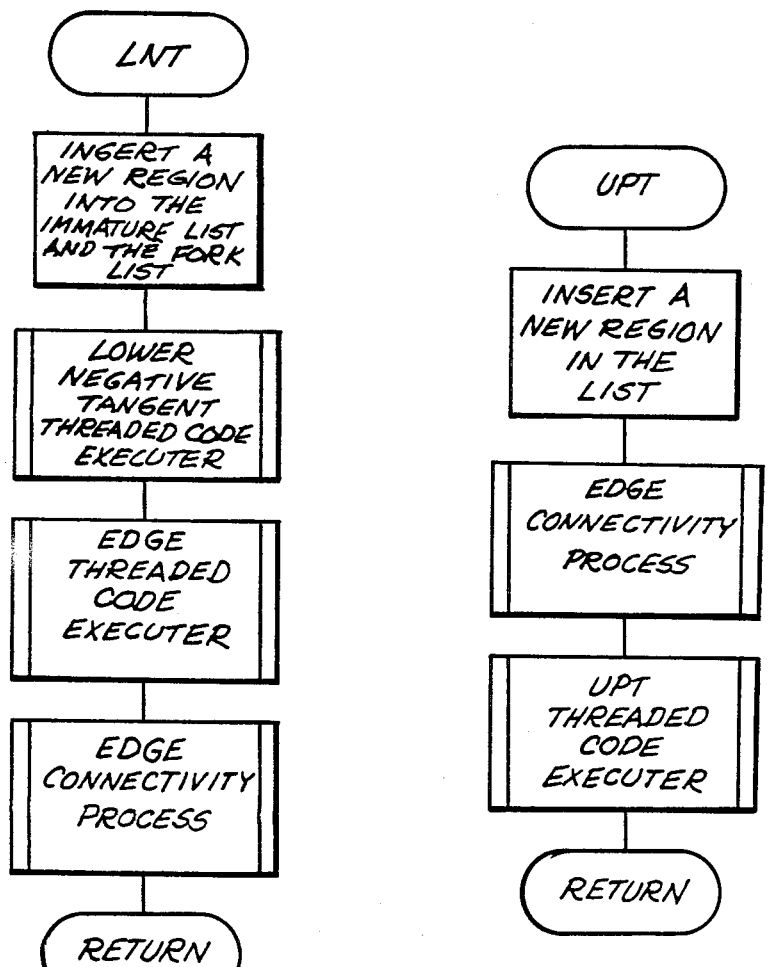

There exists some number of image lines, or a period of imagery, after which host processors have a need to know what the processed data has engendered. This is a time which we call Report Period Processing. (FIG. 8H)

In summary, then, there are the following Measurement and Process Events (times).
1. FMEAS (Measurement (5 events)).
2. EOFEA (End of Feature Processing).
3. FPRAM (Full Processing RAM Processing).
4. EORPP (End of Report Period Processing).

In processing a list of measurements is downloaded to the host processor. For example, the host might want to know the boundaries of a Ferets box for a particle and its area. A 'string' used to prescribe this processing is:

LIST( FP(0),FP(180),FP(90),FP(−90),AIH )

where FP stands for Ferets Point and the argument is an angle. AIH stands for Area Including Holes. This type of processing we will call Feature Vector Processing (FVP).

Another type of processing is to receive and histogram various particle sizes and perform some statistics on their sizes. Then at the end of a report period, the results will be uploaded to the host processor. This type of processing we will call Report Period Processing (RPP).

Another type of processing involves taking one or more measurements or numbers and performing some arithmetic expression on them. This type of processing we will call Derived Measurement Processing (DMP).

And finally, another type of processing involves taking a measurement or derived measurement and determining whether the process chain will be continued or aborted. This type of processing we will call Measurement Selection Processing (MSP).

Summary of Types of Processing

1. FVP (Feature Vector Processing).
2. RPP (Report Period Processing)
3. DMP (Derived Measurement Processing).
4. MSP (Measurement Selection Processing).

Processing is done at EOFEA, EORPP, PPRAM, and FMEAS times. MEAS, FVP, RPP, DMP and MSP processing occurs for MEAS processing at LPT time, when a feature is discovered to be mature, the address of the data is generated and placed in each measurement MRPPB (mature region processing procedure block) at the MRDATAR displacement. This is performed by the MEAS-type EOFEA processing which is caused to execute by the EOFEA Executer. Each measurement has a MEAS-type MRPPB. The relevant data in the mature region will be addressed by the MRDATAR of the appropriate MRPPB. Each MEAS-type MRPPB must be executed before any SUPERIOR MRPPBs.

Various operations are performed on the codes which cause measurement data to be accumulated in the immature region. Each measurement has an IMRMPB (immature reqion measurement processing block). In this structure are addresses of executable code for upt, unt, lnt, lpt, and edge events. In addition is the displacement into an immature region for the data associated with that measurement. In this way, the 'string' prescribing the measurements which are to be performed result in the measurement and process compiler (MPC) computing the displacement into the immature region for each measurement.

A MRPPB (mature region processing procedure block) is a collection of data which contains addresses for executable code for EOFEA, EORPP, and FPRAM processing times. It also contains an address at displacement MRSCALR to support data users for its data. A processing block who uses data from another (subordinate) processing block accesses this data by executing the code at the subordinate's address contained at the MRSCALR displacement. In addition to these executable code addresses, the MRPPB contains a list of subordinate MRPPB addresses, and also an address where its data is stored. This address is located at displacement MRDATAR in the MRPPB. The MRPPB looks like this:

```
            OFFSET 0
MRID     DS.L 1    4 CHAR OF ID
MRSF     DS.W 1    SIZE OF THIS BLOCK
MRHLK    DS.L 1    LINK TO THE NEXT BLOCK
MREOFEA  DS.L 1    ADDRESS OF EOFEA CODE
MREORPP  DS.L 1    ADDRESS OF EORPP CODE
MRFPRAM  DS.L 1    ADDRESS OF FPRAM CODE
MRSCALR  DS.L 1    ADDRESS OF SCALAR CODE
MRDATAR  DS.L 1    ADDRESS OF 'MY' DATA
MRSUBOR  DS.L 1    ADDRESS LIST OF SUBOR.
```

MRPDB stands for Mature Region Processing Definition Block. This block contains information used by the MPC to form a MRPPB. MRPPBs are computed by the MPC using the 'string' and the MRPDBs. An example may help. Consider the 'string'

LIST( AIH DIV SQR( PR ) )

which means to download to the HOST the one-element feature vector which is the result of dividing the area including holes by the square of perimeter.

Taking the situation from the point of view of the MRpPB for "DIV" (a DMP-type process). The addresses for the code come from the MRPDB, but the rest of the MRPPB is specific to this particular instance of "DIV". The subordinates are the "AIH" MEAS-type MRPPB, and the "SQR" DMP-type MRPPB. The superior to "DIV" is "LIST", a FVP-type MRPPB.

When MESCALR executable routines are called, the data at the subordinate MRDATAR address must be valid. This means that the subordinate's EOFEA processing must be called prior to the superior's EOFEA processing.

In the MPC, in the simple 'string' cited earlier, the superior processes are in outer parenthetical groups. The same considerations that lead to evaluation of arithmetic or logical expressions apply to this situation.

Constants are also handled. For example, 4*pi*AIH can be evaluated. A constant is a process. It has a process definition block with scalar code to return the instance of the constant which is scanned from the string. There is only one MRPDB and one MRPPB tor every instance of a constant.

The following are examples of measurements and processes:

| MEASUREMENTS | DERIVED MEASUREMENTS | REPORTS |
|---|---|---|
| AREA INCL HOLES | ADD | TOTAL |
| AREA EXCL HOLES | SUB | STATISTICS |
| PERIM INCL HOLES | MUL | HISTOGRAM |
| DIRECTED FERETS | DIV | LIST |
| X_CENTROID | SQR | |
| Y_CENTROID | PWR | |
| PROJ LENGTH | SQRT | |
| LONGEST DIMENSION | FEA COUNT | |
| BREADTH | | |
| COUNT OF HOLES | | |
| EULER NUMBER | | |
| CONVEX PERIMETER | | SELECTIONS |
| ORIENTATION OF LD | GT | IF | GE |
| ORIENTATION OF BR | LT | NOT | LE |
| DIRECTED TANGENT POINT | EQ | AND | OR |

The following is an example of codes which can be used. The EOFEA Executer is

```
*Executer for End of Feature Time
*
EOFEAEX    EQU   *
           MOVEA.L  A2,-(A7)           save caller's A2
EOFEA_GO   MOVEA.L  MREOFEA(A2),A3     Address of code
           JSR      (A3)               Call the code
           BNE.S    EOFEAQ             Quit - broken chain
           MOVEA.L  MRHLI(A2),A2
           CMPA.L   #0,A2              Test for the end
           BNE.S    EOFEA_GO
EOFEAQ     MOVEA.L  (A7)+,A2           Recover A2
           RTS
```

The following is an example of Derived Measurement Process, namely the EOFEA DIV process code

```
*
EOFDIV   LEA      MRSUBOR(A2),A3    Address the list of
         MOVEA.L  (A3),A4           subordinate MRPPBs
         MOVEA.L  MRSCALR(A4),A3    ..First subordinate
         JSR      (A3)
         MOVE.L   D0,D1             ..returns arg
         ADDQ.L   #4,A4             ..Second subordinate
         MOVEA.L  MRSCALR(A4),A3
         JSR      (A3)
         DIVU     D0,D1
         MOVEA.L  MRDATAR(A2),A3
         MOVE.L   D0,(A3)           ..'My' Data
         MOVE     #1<< 2,CCR        ..don't break the chain
         RTS
```

An IMRMPB (immature region measurement processing block) is a collection of data which contains addresses for executable code for the measurement times, and displacements to the data which is located within the immature region. The IMRMPB code can be as follows:

|         | OFFSET  | 0                           |
|---------|---------|-----------------------------|
| IMRID   | DS.L 1  | 4 char of ID                |
| IMRSF   | DS.W 1  | size of this block          |
| IMRHLK  | DS.L 1  | address of the next IMRMPB  |
| IMRUPT  | DS.L 1  | addr. UPT code              |
| IMRLPT  | DS.L 1  | addr. LPT code              |
| IMRUNT  | DS.L 1  | addr. UNT code              |
| IMRLNT  | DS.L 1  | addr. LNT code              |
| IMRDATAIX | DS.W 1 | index of data within the Rgn |

Examples of code involving the measurement processing are set forth below:

```
*
* Code supporting the execution of any and all measurements
* at UPT time.
*     Registers:    D0 D1 D2 D3 D4 D5 D6 D7 A0 A1 A2 A3 A4 A5 A6
*     Entry:         *  *                    *
*     Used:             *                       *  *  *
*     Note:      All registers are saved and restored.
UPTREGS     REG       D0-D2/A0-A3
UPTMEAS     MOVEM.L   UPTREGS,-(SP)
            LEA       FMEASADR(PC),A1    Addr. of the meas chain
UPT_AGAIN   MOVEA.L   IMRUPT(A1),A3      Associated code
            MOVE.W    IMDATAIX(A1),D2    Data area index
            LEA       0(D2.W,A0),A2      Computed Data address
            JSR       (A3)
            MOVEA.L   IMRHLK(A1),A1      Next measurement
            CMPA.L    #0,A1
            BNE.S     UPT_AGAIN
            MOVEM.L   (SP)+,UPTREGS
            RTS
*
* Code which creates Area including hole data at UPT
* D0,D1 is the intercept, A2 is the data area.
AIHREGS     REG       D1,A0
AIHUPT      MOVEM.L   AIHREGS,-(SP)
            SUB.L     D0,D1              Length of intercept
            LEA       MPAR(PC),A0        Measurement parameter area
            MULU      V_RAS(A0),D1       Multiply by raster vertical
            MOVE.L    D1,(A2)            to calculate area/store it.
            MOVEM.L   (SP)+,AIHREGS
            RTS
```

We claim:

1. A system for the analysis of a continuous process which comprises sensor means responsive to the process for continuously generating signals, means for digitizing said signals and providing a continuous flow of first digital signals corresponding thereto, means operative continuously and in parallel upon said first digital signals for reducing said first digital signals into a continuous flow of second digital signals occurring at a reduced rate from the continuous flow of first digital signals and representing predetermined events in said process, and means responsive to and operative continuously upon said second digital signals for providing outputs representing the analysis of certain defects in said process represented by said events.

2. The system according to claim 1 wherein said means for reducing said first digital signals into said continuous flow of second digital signals comprises means for encoding said first digital signal into digital outputs representing said events and the location thereof in said process, and at least one array of parallel digital processors operative concurrently in real time on said outputs for providing said second digital signals.

3. The system according to claim 2 wherein said reducing means further comprises memory means for retaining a plurality of successive ones of said digital outputs, and means for transferring successive groups of said outputs sequentially to different ones of said processors in said array.

4. The system according to claim 1 wherein said process comprises production of a continuous web medium, said sensor means includes means for scanning said medium to cover continuous, contiguous lines thereon each line containing a multiplicity of pixels, said digitizing means including means for providing said first digital signals representing successive ones of said pixels, said means for reducing said first digital signals comprising at least one array containing a plurality of digital signal processors for processing different groups of said first digital signals concurrently to provide said second digital signals.

5. The system according to claim 4 wherein said reducing means comprises means responsive to said events for encoding said first digital signals into digital outputs representing the occurrence and location of said events representing defects in said web, and means for allocating successive ones of said groups of said outputs to different ones of said digital signal processors for concurrent operation thereon.

6. The system according to claim 5 further comprising means operative upon groups of said first digital signals for processing said first digital signals to provide digital signals representing each pixel enhanced to characterize said defects, said encoding means being responsive to said enhanced digital signals.

7. The system according to claim 6 wherein said enhanced digital signal providing means comprises an array of units for processing continuously successive groups of said first digital signals representing pixels disposed consecutively on different ones of plurality of said lines to convolve said successive first digital signal groups to provide said enhanced digital signals.

8. The system according to claim 7 wherein said array comprises a plurality of finite impulse response (FIR) units each providing multi-bit digital signals, each of said FIR units corresponding to a different one of said plurality of lines, means for applying digital signals from said different lines to the FIR unit corresponding thereto, and means for adding said multi-bit digital signals to provided said enhanced digital signals.

9. The system according to claim 8 wherein each of said FIR units comprises a plurality of multiplier accumulator stages connected in tandem for deriving the composite running sum of each of said first digital signals and a plurality of different coefficients, said running sums each providing a different one of said multi-bit digital signals.

10. The system according to claim 5 wherein said encoding means comprises means responsive to said first digital signals for detecting the occurrence of said defects, means operated by said defect detecting means and responsive to the occurrence of said pixel representing first digital signals for providing said digital outputs corresponding to the number of pixels between successive ones of said defects.

11. The system according to claim 10 wherein said encoding means further comprises means for also providing one said digital outputs when a predetermined number of said pixel representing first digital signals occur after occurrence of one of said digital outputs corresponding to one of said defects.

12. The system according to claim 10 wherein means are provided operative upon groups of said first digital signals for providing digital signals representing each pixel enhanced to characterize said defects, said enhanced digital signal providing means comprising an array having a plurality of finite impulse response (FIR) units each providing a multi-bit digital signal, each of said FIR units corresponding to a different one of said lines, means for applying digital signals from different ones of said lines to the FIR unit corresponding thereto, means for adding said multi-bit digital signals to provide said enhanced digital signals, said detecting means comprising means for translating said enhanced digital signals into digital signals coded to characterize said defects and the occurrence thereof.

13. The system according to claim 12 wherein said means operated by said defect detecting means comprises run length encoder means for providing said digital outputs corresponding to counts of said pixel representing first digital signals accumulated between said coded defect characterizing digital signals.

14. The system according to claim 13 further comprising memory means for storing a plurality of consecutively occurring ones of said coded defect characterizing signals, and said allocating means being operative upon successive groups of said consecutively occurring coded defect characterizing signals stored in said memory means for allocating them to different ones of said digital signal processors.

15. The system according to claim 14 wherein said digital signal processors include mean responsive to the numbers of pixels and the defect characterization information contained in said outputs for providing as said analysis data representing measurements of said defects and the location thereof with respect to said web.

16. The system according to claim 10 wherein said digital signal processors include means responsive to the numbers of pixels and the defect characterization information contained in said outputs for providing as said analysis data representing measurements of said defects and the location thereof with respect to said web.

17. The system according to claim 4 wherein said digitizing means comprises analog to digital converter means operative at the rate of scanning of said pixels to provide pixel representing digital signal bytes, memory means for continuous storing a plurality of said bytes which occur successively, and means for accessing one at a time and in the sequence stored in said memory each of said bytes which are stored in said memory asynchronously as a rate controlled by said reducing means to provide said first digital signals.

18. The system according to claim 17 wherein said accessing means comprises a continuous flow data bus interconnecting said digitizing and reducing means, and direct memory access processing means operated by said bus when it is available to transmit data to said reducing means for reading out said bytes one at a time in the order stored in said memory means from said memory means.

* * * * *